US008318961B2

(12) United States Patent
Wolf

(10) Patent No.: US 8,318,961 B2
(45) Date of Patent: Nov. 27, 2012

(54) OLIGOMERS OF CHOLESTEROL, CHOLESTEROL SULPHATE AND CHOLESTEROL ESTERS AND ALSO DRUGS CONTAINING THESE

(75) Inventor: Hans-Uwe Wolf, Neu-Ulm (DE)

(73) Assignee: PLT Patent & Licensing Trading Ltd., Cambridge (GB)

( * ) Notice: Subject to any disclaimer, the term of this patent is extended or adjusted under 35 U.S.C. 154(b) by 998 days.

(21) Appl. No.: 11/995,256

(22) PCT Filed: Jul. 11, 2006

(86) PCT No.: PCT/EP2006/006772

§ 371 (c)(1),
(2), (4) Date: Nov. 10, 2008

(87) PCT Pub. No.: WO2007/006549

PCT Pub. Date: Jan. 18, 2007

(65) Prior Publication Data

US 2009/0105199 A1 Apr. 23, 2009

(30) Foreign Application Priority Data

Jul. 11, 2005 (DE) ........................ 10 2005 032 268

(51) Int. Cl.
*C07J 9/00* (2006.01)
*A61K 9/00* (2006.01)
*A61K 8/02* (2006.01)

(52) U.S. Cl. ......................... 552/544; 424/400; 424/401

(58) Field of Classification Search .................. 552/544; 424/400, 401

See application file for complete search history.

(56) References Cited

U.S. PATENT DOCUMENTS

| | | | |
|---|---|---|---|
| 2,520,980 | A | 9/1950 | Terkel et al. |
| 5,153,340 | A | 10/1992 | Ichikawa et al. |
| 6,447,790 | B1 | 9/2002 | Ishii et al. |

FOREIGN PATENT DOCUMENTS

| | | |
|---|---|---|
| CN | 1793160 | 6/2006 |
| JP | 05-286844 | 11/1993 |
| JP | 05-320188 | 12/1993 |
| JP | 06-287128 | 10/1994 |
| JP | 07-238009 | 9/1995 |
| WO | WO 9965462 | * 12/1999 |

OTHER PUBLICATIONS

Proksch E, Holleran WM, Menon GK, Elias PM, and Feingold KR (1993) : Brit J Dermtol 128 (5) : 473-482.
Man MQM, Feingold KR, Thornfeldt CR, Elias PM (1996): J Invest Dermatol 106(5): 1096-1101.
Di Nardo A, Wertz P, Gianetti A, and Seidenari S (1998): Acta Derm Vererol 78(1): 27-30.
Bouwstra J, Pilgram G, Gooris G, Koerten H, and Ponec M (2001) Skin Pharmacol Appl Skin Physiol 14 (Supp. 1): 52-62.
Arikawa J, Ishibashi M, Kawashima M, Takagi Y, Ichikawa Y, and Imokawa G (2003): J Invest Dermatol 119(2); 433-439.
Yarosh DB, Both D, and Brown D (2000) Hormone Research 54: 318-321.
Barlag KE, Goerz G, Ruzicka T, and Schurer NY (1995): BR J Dermatol 133(4): 639-643.
Zettersten E, Man MQ, Sato J, Denda M, Farrell A, Ghadially R, et al. (1998): J Invest Dermatol 111(5): 784-790.
Claudy A (2003): Pathol Biol (Paris) 51 (5): 260-263.
Tanno O, Ota Y, Kitamura N, Katsube T, Inoue S (2000): British J Dermatol 143(3): 524-531.
Hatfeld RM and Fung LW (1999): Biochemistry 38(2): 784 791.
International Search Report corresponding to PCT/EP2006/006772, dated Jan. 10, 2007.
English language abstract corresponding to JP 06-287128.
English language abstract corresponding to JP 05-320188.
English language abstract corresponding to JP 05-286844.
English language abstract corresponding to JP 07-238009.
English language abstract corresponding to CN 1793160.

* cited by examiner

*Primary Examiner* — Barabara P Badio

(74) *Attorney, Agent, or Firm* — Millen, White, Zelano & Branigan, P.C.

(57) ABSTRACT

The invention relates to new substances which are derived from cholesterol, cholesterol sulphate and cholesterol esters of a natural, semi-synthetic or synthetic origin in that they represent oligomers with a specific type of cross-linkage of the starting substances based on cholesterol.

8 Claims, 4 Drawing Sheets

Figure 1:
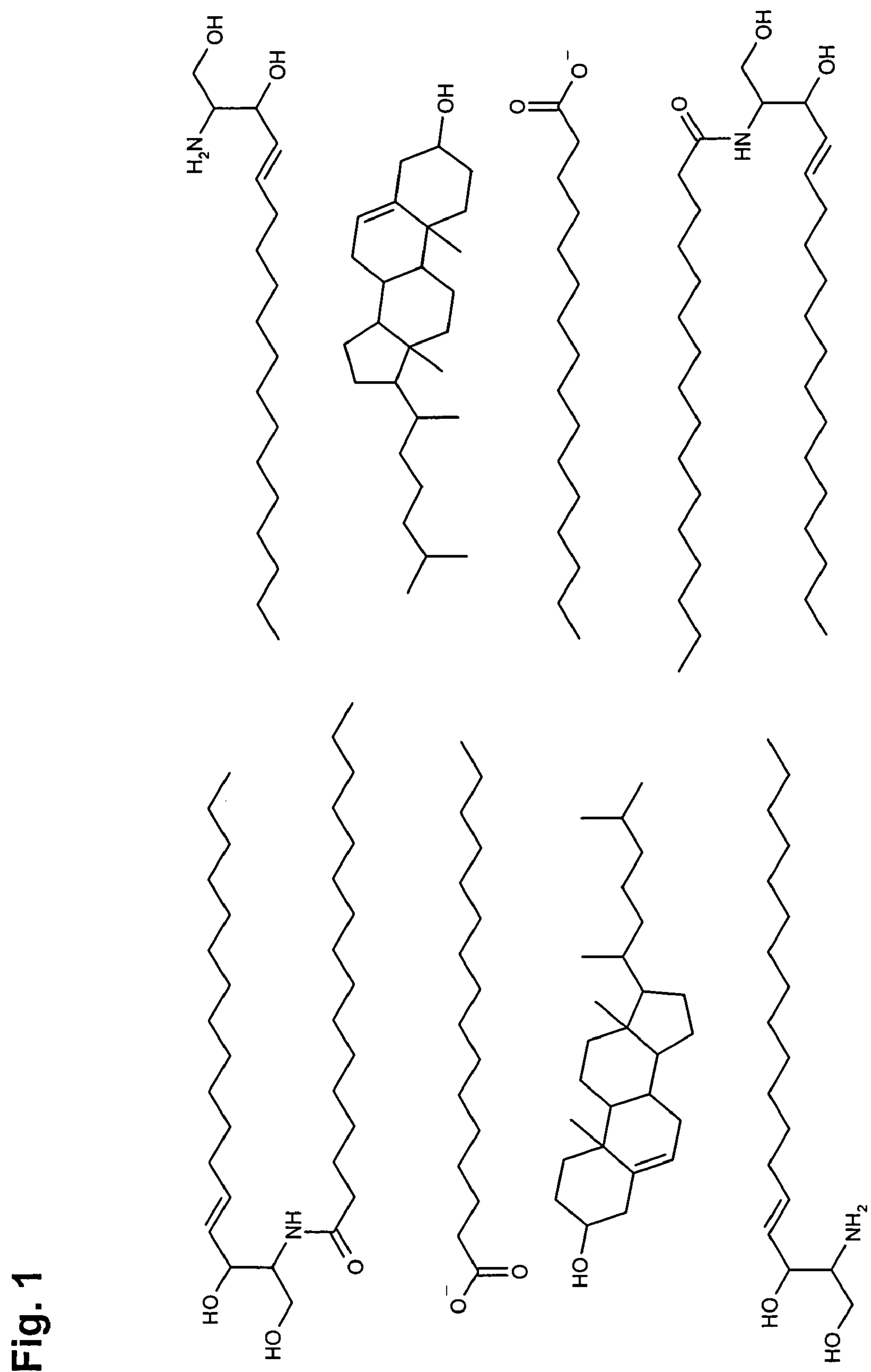

OLIGOMERS OF CHOLESTEROL, CHOLESTEROL SULPHATE AND CHOLESTEROL ESTERS AND ALSO DRUGS CONTAINING THESE

The invention relates to new substances which are derived from cholesterol, cholesterol sulphate and cholesterol esters of a natural, semi-synthetic or synthetic origin in that they represent oligomers with a specific type of cross-linkage of the starting substances based on cholesterol.

Basically, all biological membranes, in particular cell membranes, contain so-called lipids and lipid-analogous substances as essential components which structurally are constructed differently but which are similar in their construction principle. The similarity in principle of the structure resides in the fact that they are constructed from a hydrophobic and a hydrophilic component.

In the case of lipid-analogous substances from the group of cholesterol, cholesterol sulphate and cholesterol esters, the hydrophobic molecule region comprises the ring system of cyclopentanoperhydrophenanthrene with the 1,5-dimethylhexyl radical in position 17, whilst the hydrophilic molecule region is essentially a hydroxyl group in position 3. Hence cholesterol belongs in the broadest sense to the lipid-analogous substances. By analogy, the same applies to the compounds, cholesterol sulphate and cholesterol ester, which are derived therefrom.

The amphiphilic structure of the lipid-analogous substances, i.e. the simultaneous presence of a (strongly) hydrophobic and a hydrophilic, polar component of the molecule structure, leads to the lipid-analogous substances in an aqueous phase together with lipids arranging themselves spontaneously to form a lipid double layer, a so-called "lipid bilayer" which represents inter alia the basis of the structure of biological membranes. The structural principle of this bilayer is the same for all lipids and lipid-analogous substances: they are arranged in two parallel layers which are situated closely together, the hydrophobic radicals of the relevant molecules respectively being situated directly opposite and coming into contact. Hence they form the hydrophobic inner region of the membrane bilayer, whilst the hydrophilic radicals are in contact on both sides of the lipid bilayer with the aqueous phase. The tendency to form this lipid bilayer resides both within and also outwith an organism, e.g. in an aqueous system in which the properties of the lipid bilayers can be examined in experimental arrangements designed specially for this purpose.

Although the structure of the lipid bilayer is formed spontaneously in an organism and has a significant stability, the possibility exists for example in the presence of a lipid metabolism disorder that a biological membrane loses a part of its lipid components because these molecules are formed either too slowly and/or in an inadequate amount or are metabolised (too rapidly) and hence are withdrawn from the membrane structure, or the relevant membranes are depleted of these components in the course of a pathological disorder of the membrane structure and function. A well known example of changes of this type is the depletion in the lipid bilayers of the stratum corneum of human skin of fatty acids and/or of cholesterol, cholesterol sulphate and/or cholesterol esters. It was established in various works that this group of cholesterol compounds has considerable importance for the construction and the function for the stratum corneum (Proksch E, Holleran W M, Menon G K, Elias P M, and Feingold K R (1993): *Brit J Dermatol* 128 (5): 473-482; Man M Q M, Feingold K R, Thornfeldt C R, Elias P M (1996): *J Invest Dermatol* 106 (5): 1096-1101; Di Nardo A, Wertz P, Gianetti A, and Seidenari S (1998): *Acta Derm Venerol* 78 (1): 27-30; Bouwstra J, Pilgram G, Gooris G, Koerten H, and Ponec M (2001): *Skin Pharmacol Appl Skin Physiol* 14 (Supp. 1): 52-62).

Various skin changes and skin diseases are based on changes in the lipid composition of the stratum corneum layer in human skin. These changes in the sense of a lipid loss lead to a more or less severely reduced water binding capacity of the relevant skin parts. Skin changes and skin diseases of this type are for example:

1. atopic dermatitis
2. "dry" skin xerosis, xeroderma
3. dyshidrotic eczema
4. chronic cumulative toxic contact eczema
5. ageing skin
6. skin severely affected by UV light
7. sebostasis
8. keratinisation disorders In particular in the field of clinical medicine, it is desirable in the mentioned cases of diseases to change and/or to stabilise the structure of the biological membrane present in the organism, i.e. the lipid bilayers, in a suitable manner.

As cited above already, biological membranes of a large number of cells are constructed from a lipid bilayer which represents an effective barrier relative to the extracellular space. This also applies to the stratum corneum of the skin. In humans, this skin structure comprises a plurality of layers of keratinised corneocytes which are embedded in a lipid matrix of a highly ordered lamellar structure. These lipid bilayers essentially contain cholesterol and also ceramides and fatty acids, such as e.g. palmitic acid.

According to recent knowledge relating to the pathological mechanism of atopical dermatitis (Arikawa J, Ishibashi M, Kawashima M, Takagi Y, Ichikawa Y, and Imokawa G (2002): *J Invest Dermatol* 119 (2): 433-439) and related diseases (Yarosh D B, Both D, and Brown D (2000) *Hormone Research* 54: 318-321), the cause of the susceptibility of the skin in the case of a disease of this type is inter alia a changed lipid metabolism or reduced lipid content of the stratum corneum. These changes relate inter alia to the cholesterol content of the skin. Thus there were revealed, in the case of atopic dermatitis but also in the case of other skin diseases, as in psoriasis, in (lamellar) ichthyosis and in contact dermatitis, reduced or altered contents of free cholesterol or cholesterol compounds or a disordered cholesterol sulphate/cholesterol relation in the skin of patients (Barlag K E, Goerz G, Ruzicka T, and Schurer N Y (1995): *Br J Dermatol* 133 (4): 639-643; Zettersten E, Man M Q, Sato J, Denda M, Farrell A, Ghadially R, et al. (1998): *J Invest Dermatol* 111 (5): 784-790; Claudy A (2003): *Pathol Biol* (*Paris*) 51 (5): 260-263).

The physiological composition of the membrane lipids of the stratum corneum of human skin is however still of essential importance for the normal structure and function of the skin for a second reason. The presence of an adequate content of these lipids ensures the unrestricted capacity of the skin for binding a physiological quantity of water. The loss of a part of the stratum corneum lipids therefore leads to a restriction in the water binding capacity, which is expressed in the so-called transepidermal water loss of the skin. The consequence thereof is the occurrence of a "dry" and wrinkled skin which can be observed frequently but not exclusively in particular in old age.

The current possibilities for alleviating the symptoms and consequences of the mentioned skin diseases, in particular atopical dermatitis (at present a cure is still not possible), are still very limited. Topical application of special glucocorticoids and immunosuppressive active substances is associated with significant risks because of the simultaneous toxicity of these substances. Specific corticoids even cause an almost counter-productive effect in that they lead to a loss of ceramides, cholesterol and free fatty acids.

Taking into account the current state of knowledge about the importance of a physiological lipid composition of the stratum corneum membranes, it is logical to attempt to compensate for any deficits in membrane lipids which exist in the stratum corneum by means of an exogenous supply. In practice, at attempt is made to supply the missing lipids, e.g. ceramides and free fatty acids, to the changed or diseased skin with the help of ointments, creams and the like. This is effected for example by lipid preparations which are specially formulated for this purpose, including ceramides and free fatty acids, inter alia by using liposomes as carrier systems. Numerous products with a composition of this type have become available commercially in the meantime for the therapy of the mentioned skin diseases.

The therapeutic measures portrayed here should of course be regarded as correct in principle since they logically attempt to compensate for the deficits existing in the stratum corneum of lipids and lipid-analogue substances. Empirical knowledge established with these therapeutic measures during the last few years reveal however, that despite the correctness of the therapy approach in principle, the results of these curative treatments are in no way convincing. In part, the success of the implemented measures is unreliable. Even if an approximately acceptable success of the curative treatment arises, a curative treatment of this type has at least two grave disadvantages:

The extent of the successful cure is not so great that it can be called complete recovery of the diseased skin.

In order to ensure to some extent an acceptable successful cure of the skin over a fairly long period of time, the mentioned lipids and lipid-analogue substances must be supplied permanently to the skin at short time intervals.

Both disadvantages can be attributed to a common cause. The mentioned lipids or lipid-analogous substances (apart from cholesterol and also for example ceramides and free fatty acids) are not static but dynamic components of the skin. This means that the membrane components are in equilibrium with the non-membrane-bonded lipid pool of the organism. In this dynamic equilibrium, the individual lipid components can be rapidly exchanged. In the lipid pool itself, they represent intermediate products of a reaction sequence in which the lipids required by the skin, e.g. from nutritional fats (triglycerides) or other nutritional components, are made available and, after detection of their function as membrane component of the stratum corneum, are subsequently included in the fatty acid metabolism. This also applies in principle to cholesterol.

This reaction sequence represents a steady state in which a specific quantity of the mentioned components is changed metabolically by the effect of specific enzymes step by step. Hence a specific throughput of substances occurs. The lipids supplied exogenously as skin therapeutic agents are included in this reaction sequence. If there is a priori disruption in such a reaction sequence which then leads to a pathological lipid composition of the stratum corneum, then it is to be expected that the exogenous supply of lipids in the form of a therapeutic agent can change nothing fundamentally or not much in this pathological state since the exogenously supplied lipid component of the organism is further processed in the same way as is the case with the lipid component available endogenously. A successful cure with the therapeutic possibilities available at present is therefore dependent to a large extent upon the relevant therapeutic replacement substances being able to penetrate into the skin more rapidly than they are included in the existing physiological degradation steps and them being supplied continuously over a fairly long period of time, in the extreme case for life.

The present problem cannot be readily resolved. Certain physiological and physical-chemical or biochemical limits are set upon the rate of absorption of lipids and lipid-analogous substances into the stratum corneum, for example with respect to the diffusion rate of the active substances supplied as therapeutic agents. This rate cannot be increased, at least not according to the current state of knowledge, to the extent required for a permanent successful cure.

There are involved in the mentioned reaction sequences of the lipid synthesis and degradation, respectively synthesising and metabolising enzymes which have the function of the lipid synthesis and degradation. In order to improve the success of a therapy, the synthesising enzymes would require to be activated but the metabolising enzymes to be inhibited. Activation of a synthesising enzyme is obviously possible in human keratinocyte cultures (Tanno O, Ota Y, Kitamura N, Katsube T, Inoue S (2000): *British J Dermatol* 143 (3): 524-531), in which the biosynthesis of different stratum corneum lipids is significantly increased by nicotinamide. However it is uncertain whether this is also possible in the entire human organism and whether the side-effects occurring during such a therapy are tolerable. On the other hand, the lipid-metabolising enzyme cannot be influenced by exogenous measures or not without serious problems in the sense of reducing or inhibiting their activity since for this purpose the required specificity for the enzyme restriction is lacking.

In order to resolve the described problem, it is necessary basically to apply other principles in order to increase the therapeutic effectiveness of exogenously supplied lipid replacement or lipid-analogous substances.

The object of the present invention is therefore to provide compounds by means of which biological membranes present in the organism can be modified or stabilised in a suitable manner.

This object is achieved with respect to the described oligomers by the features of oligomers of at least two cholesterol monomers selected from the group comprising cholesterol, cholesterol sulphate and cholesterol esters, the monomers being bonded to each other covalently via at least one chain end by a spacer or by a bond, with respect to the human or veterinary drug containing oligomers described herein, with respect to the cosmetic or body care agent containing oligomers described herein, with respect to the use as a drug for the prophylaxis and therapy of diseases in which a disorder of the skin is present with respect to the content of cholesterol, cholesterol sulphate and/or cholesterol esters. The further aspects described below reveal advantageous developments: regarding the oligomers described herein, which are characterized in that the oligomers are dimers, trimers, tetramers, pentamers, hexamers and/or higher oligomers; or are characterized in that the cholesterol monomers are of a natural, semi-synthetic or synthetic origin; or are characterized in that two adjacent monomers of cholesterol, of cholesterol sulphate and of cholesterol esters are connected respectively via their hydrophobic end; or are characterized in that two adjacent monomers of cholesterol, of cholesterol sulphate and of cholesterol esters are bonded to each other covalently respectively at their hydrophobic end via an intramembrane spacer; or are characterized in that the intramembrane spacer is hydrophobic; or are characterized in that the intramembrane spacer comprises one or more carbon-, oxygen- and/or nitrogen atoms; or are characterized in that two adjacent monomers of cholesterol, of cholesterol sulphate and of cholesterol esters are bonded covalently respectively via their hydrophilic end; or are characterized in that the monomers of cholesterol, of cholesterol sulphate and of cholesterol esters are bonded respectively via the ω-position carbon atom of the 1,5-dimethylhexyl radical; or are characterized in that two adjacent monomers of cholesterol, of cholesterol sulphate and of cholesterol esters are connected to each other respectively at their hydrophilic end by means of an extramembrane spacer; or are characterized in that the extramembrane spacer is hydrophilic; or are chacterised in that the extramembrane spacer contains as structural components, glycerine, hydroxylated dicarboxylic acids, amino acids, carbohydrate components, in particular monosaccharides, disaccharides or oligosaccharides, mevalonic acid and/or pyrrolidone carboxylic acid; or regarding the use thereof as a drug described herein, which are characterized in that a disorder of the composition of the stratum corneum of the skin is present with respect to the content of cholesterol, cholesterol sulphate and/or cholesterol esters; or are characterized in that a disorder of the stability and composition of the cell membrane of the liver is present with respect to the content thereof of cholesterol, cholesterol sulphate and/or cholesterol esters as a result of the damaging effect of liver cell poisons; or are characterized in that a disorder of the stability and composition of the cell membrane of nerve cells is present with respect to the content thereof of cholesterol, cholesterol sulphate and/or cholesterol esters, inter alia in the case of neuronopathies, axonopathies and myelinopathies; or are characterized in that, in the case of a fat metabolism disorder with a subsequent disorder of the composition of the cell membrane of blood and other cells in the sense of undesired storage of oxidation products of cholesterol, the oligomers according to the invention of cholesterol, of cholesterol sulphate and/or of cholesterol esters serve to reduce the high thrombotic, atherosclerotic and cardiovascular risk.

The compounds proposed according to the invention therefore comprise oligomers of cholesterol, cholesterol sulphate and cholesterol esters. There is understood by oligomers in the sense of the invention the cross-linking of two to twelve monomers. There are preferred here in particular dimers, tetramers, hexamers and octamers.

The term "dimerisation" is used according to the present invention also when not only is the direct connection of two molecules involved (with precise doubling of the number of the respectively contained atoms) but also when the two original individual molecules are connected by a short molecular bridge in the sense of a so-called spacer. According to the present invention, the term "oligomers" is also used when these compounds involve not only the connection of a plurality of molecules but also when these are connected by molecular bridges in the form of different spacers.

The structural elements of the oligomers according to the invention thereby preferably comprise naturally occurring cholesterol, cholesterol sulphate and cholesterol esters.

The compounds according to the invention must fulfil the following requirements:

1. The oligomerisation must take place with formation of exclusively covalent bonds between the individual cholesterol species.
2. The basic structure of the lipid or lipid-analogous substance used which enables the formation of the lipid double membrane, should not only stay maintained but the capacity to form the double membrane should be increased because the skin damaged by the mentioned diseases in any case has only a restricted capacity to synthesise and to maintain the physiological lipid double membrane.
3. The structure of the lipid or lipid-analogous substances which are used should be changed keeping the basic structure to such an extent that they can still function only to a lesser extent as substrates for the enzymes present in the skin. This means that they are intended to be included to a significantly lesser extent than the original lipids or lipid-analogous substances in the respective enzymatic reaction sequences of their degradation reactions and hence should stay maintained as essential structural components of the stratum corneum over a longer period of time than the original lipids or lipid-analogous substances.
4. The alteration in the molecular structure should however be effected, on the other hand, only to such a small extent that such substances as are produced by the low metabolism-related conversion or degradation of the supplied oligomeric additional lipids are similar as far as possible to the intrinsic body lipids or lipid-analogous substances. In this way, the danger is significantly reduced that metabolic products with a toxic effect are produced.

The mentioned alteration of the molecular structure which fulfils the above-indicated requirements resides, in the special case of cholesterol, firstly in a dimerisation of the cholesterol, cholesterol sulphate and/or cholesterol esters used for the anticipated therapeutic effect. In order to imitate the arrangement of the cholesterol or the cholesterol compounds in a lipid double membrane, this dimerisation must be effected by cross-linking the hydrophobic 1,5-dimethylhexyl radicals of both cholesterol monomers or of the monomers of the mentioned cholesterol compounds.

Because of the structural asymmetry of the entire group of lipids and lipid-analogous substances—on one hand the fatty acid radical(s) or the 1,5-dimethylhexyl radical as hydrophobic structural component (termed "tail" in English language usage) and, on the other hand, the hydrophilic radical, in the case of cholesterol the OH group (termed "head" in English language usage)—three different types in principle can be differentiated, for example, two monomeric molecules, e.g. cholesterol, can be bonded covalently to form a dimeric molecule of this substance:

1. In the form of a "tail-to-tail" arrangement, i.e. by a covalent bond between the hydrophobic 1,5-dimethylhexyl radicals of the two cholesterol molecules to be connected. This cross-linking is effected for example by direct covalent bonding of the two end-position C-atoms (position 27) or the incorporation of a so-called intramembrane spacer between the two cholesterol molecules.
2. In the form of a "head-to-head" arrangement, i.e. by a covalent bond between the two hydrophilic, polar hydroxyl groups of the two cholesterol molecules to be connected. This cross-linking is effected for example by the incorporation of a so-called extramembrane spacer.
3. In the form of a "head-to-tail" arrangement, i.e. by a covalent bond between the hydroxyl group of the one cholesterol molecule and the hydrophobic 1,5-dimethylhexyl radical of the second cholesterol molecule.

Variant 1, i.e. the tail-to-tail arrangement, is based on the cross-linking preferably of the respectively 6)-position carbon atoms of the fatty acid radicals of both molecules to be connected, i.e. with the help of a spacer. A spacer of this type can be termed as "intradimeric" spacer, on the one hand, because of the cross-linking of two monomers to form one dimer. Since this spacer is disposed in the membrane interior during incorporation of the dimer in the biological membrane, it is however termed preferably as "intramembrane" spacer. The terms intradimeric and intramembrane should therefore be considered as equivalent with respect to their meaning.

This intramembrane spacer must have a hydrophobic nature since it is located in the hydrophobic inner region of the biological membrane. Hence a dimeric molecule is present which, because of the arrangement of its hydrophobic molecular region in the interior of the dimer, can be integrated without difficulty into a biological lipid bilayer. FIG. 2 shows the type of cross-linking and the similarity of the dimerisation product with the physiological structure of the lipid double membrane in the example of two cholesterol molecules (cf. FIG. 1).

Figure 2:
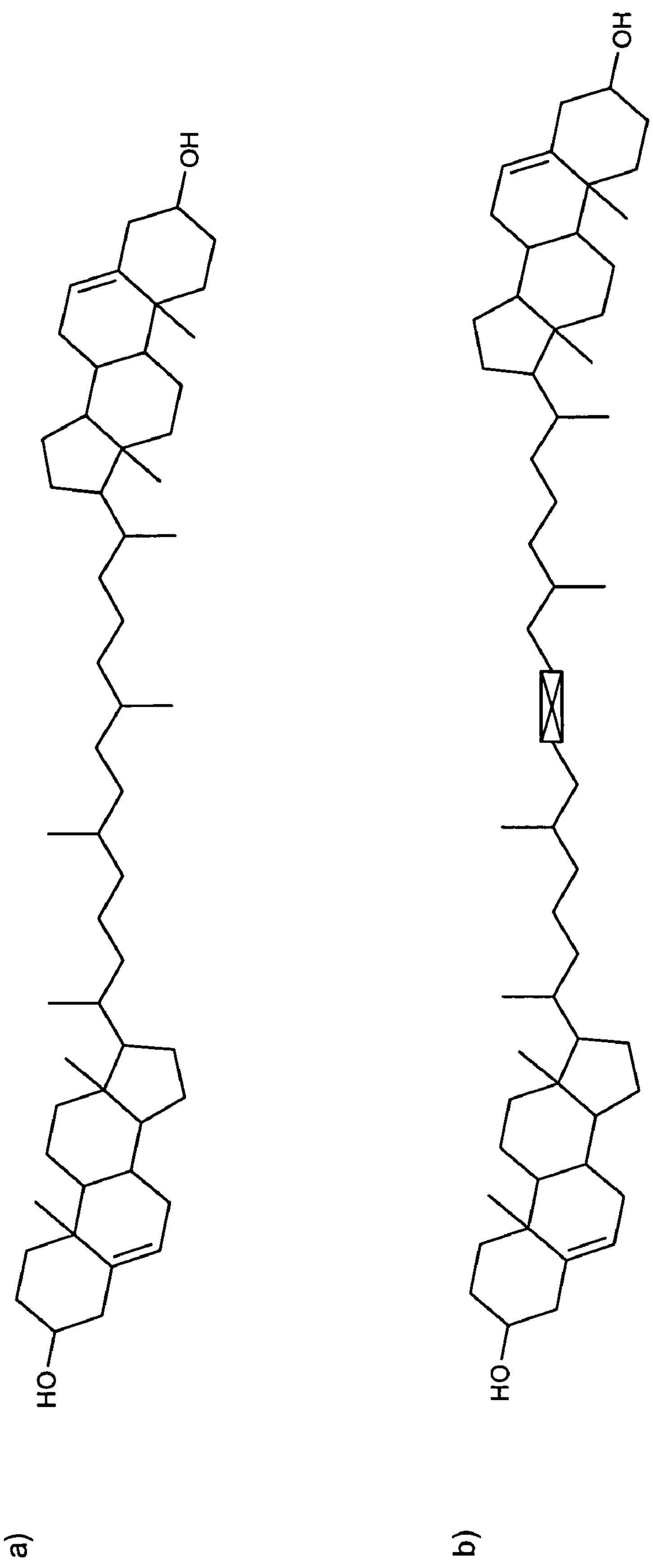

The tail-to-tail arrangement represents direct imitation of the stable arrangement of the fatty acids which is naturally present in biological membranes, as can be detected by comparison with the arrangement of the components in FIG. 1. The tail-to-tail dimer should be regarded as one of two possible basic structures for the entirety of all further cholesterol oligomers described here.

The dimerisation of the cholesterol hence leads to molecules which are inserted not only in the structure of a lipid double membrane without difficulty but which, furthermore, as a result of the presence of a covalent bond between the ω-position C-atoms of the 1,5-dimethylhexyl radicals of two oppositely situated cholesterol molecules, also contribute to significant structural stabilisation of the lipid double membrane.

Variant 2, i.e. the head-to-head dimer, has a structure which does not permit integration of the molecule into only one single lipid bilayer because the hydrophilic region of this dimeric molecule would come to be situated in the hydrophobic interior of the membrane bilayer, which would represent an extremely unstable structure which consequently is not formed spontaneously. The head-to-head dimers have however in this respect biological or medical importance in that the two cholesterol molecules which are cross-linked in this manner can be anchored in two lipid bilayers which are disposed parallel at a close spacing, each of the two cholesterol monomers being located in respectively one half of the two parallel lipid bilayers. Such lipid bilayers which are disposed at a close spacing occur for example in the myelin sheath of nerve cells.

Figure 3:
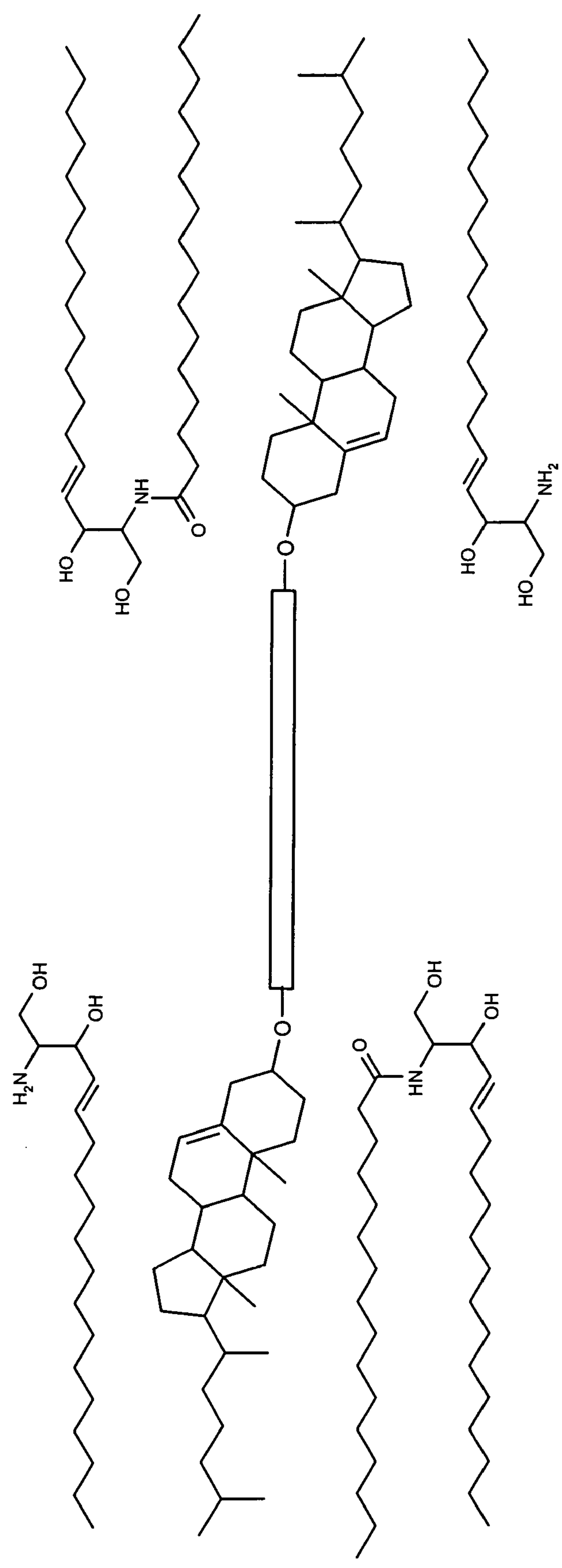

In the case of the "head-to-head" cholesterol dimer, it can be however be necessary for spatial reasons to incorporate a so-called spacer (with variable chain length) between the two monomers in order to make possible integration of the two lipid components in the two lipid bilayers even when these membranes have a specific spacing from each other (see FIG. 3 in this respect). This applies for example with the lipid bilayers of the stratum corneum of human skin which are disposed parallel.

The in principle same structure is produced by cross-linking the two molecule variants, cholesterol sulphate and cholesterol esters, which are derived from cholesterol. In the case of cholesterol sulphate, for example the free acid function of the sulphate is hereby esterified respectively with an alcoholic OH group provided on the spacer. In the case of the cholesterol esters, a covalent bond is achieved on the alkyl group of the ester in that for example the ω-position OH groups of the ester alkyl groups are cross-linked by water production to form an ether bond.

However it should be assumed that such molecules are not yet integrated optimally in two parallel-disposed lipid bilayers. Optimal integration is achieved by a molecule, in the case of which two dimers are cross-linked with each other (instead of the two monomers), said dimers then being integrated in the two parallel-disposed biological membranes. This (tetrameric) molecule then has the following structural features (see FIG. 4 in this respect):

The two dimers are constructed respectively from the monomers in the tail-to-tail arrangement by cross-linkage with the help of the above-mentioned intramembrane spacer. The cross-linkage of the two dimers is effected in the head-to-head arrangement via a further spacer which can be termed interdimeric spacer because it is disposed between two preformed dimers. Since it is located outwith the two membranes after integration of the entire molecule, it is however termed advantageously as extramembrane spacer. The two terms of interdimer and extramembrane have therefore according to the sense thereof practically the same meaning.

The extramembrane spacer, because of its position outwith the membrane, i.e. in the hydrophilic extramembrane region of the cell, must have a hydrophilic structure.

The cross-linking of the cholesterol molecule can thereby be effected in the "tail-to-tail" arrangement respectively via the hydrophobic 1,5-dimethylhexyl radical, preferably via the 6)-position carbon atom thereof, the connection being produced by a covalent bond. A second possibility resides in the fact that, instead of a covalent bond, an intramembrane spacer with a freely selectable molecular chain length is used. The intramembrane spacer thereby comprises at least one carbon atom and/or at least one heteroatom, such as e.g. oxygen or nitrogen. Preferred chain lengths of the intramembrane spacer are 1-4 atoms.

Also in the case of cross-linking of the cholesterol molecules via the "head-to-head" arrangement, this can be effected via the hydrophilic structural component by means of a covalent bond. In the case of the "head-to-head" cross-linkage, it is provided as an alternative according to the invention to use an extramembrane spacer with a freely selectable molecular chain length and composition. In the case where an extramembrane spacer is used, it is preferred that the latter is predominantly hydrophilic. Suitable structural components for a hydrophilic spacer of this type are glycerine, amino acids and/or carbohydrate components, such as monosaccharides, disaccharides, oligosaccharides etc.

Variant 3 of the lipid dimerisation has practically no biological or medical importance since a molecule of this structure cannot be integrated in any way into one or two parallel-disposed biological lipid bilayers. In all cases, at least in part hydrophilic structural components would require to be integrated into hydrophobic regions of the membranes, which would lead, as known, to very unstable structures which cannot be formed spontaneously for this reason.

Furthermore, the invention includes the possibility of producing hybrid dimers comprising cholesterol+cholesterol sulphate, cholesterol+cholesterol esters or cholesterol sulphate+cholesterol esters by oligomers of at least two cholesterol monomers selected from the group comprising cholersterol, cholesterol sulphate and cholesterol esters, the monomers being bonded to each other covalently via at least one chain end by a spacer or by a bond or by said oligomers characterized in that the oligomers are dimers, trimers, tetramers, pentamers, hexamers and/or higher oligomers and to use them in the manner described below for therapeutic purposes.

As a result of the dimerisation, ultimately particularly as a result of the oligomerisation of the cholesterol molecule and of the cholesterol compounds, it is achieved simultaneously that a dimer or oligomer of this type is degraded or converted very much more slowly by the enzymes of the cholesterol metabolism which are present in the skin than applies to the monomeric cholesterol variants. The enlargement of the molecule associated with dimerisation leads to severe reduction in the enzymatically controlled metabolisation because, in the case of the known high substrate specificity of most enzymes, the change in size of a substrate by the factor of at least 2 can allow the speed of the substrate conversion to fall considerably.

On the other hand, the resulting degradation products are so similar with respect to their general construction to naturally occurring cholesterol variants that inclusion of these compounds in the corresponding reaction sequences is possible without difficulty. Furthermore, it does not require in any way to be taken into account that the resulting oligomeric cholesterol molecules have relevant toxicity because of the great similarity to physiologically occurring monomers.

A specific degree of physiological degradability of the cholesterol dimers and oligomers which should be regarded however as significantly less than that of the monomeric cholesterol molecules is hence a desired property of the molecule according to the invention for pharmacokinetic and pharmacological reasons because, as a result, the controllability of the therapy is ensured more than if no more metabolic degradation at all were possible.

In the case where the products produced from the cholesterol by direct cross-linking of the two ω-position C-atoms of the 1,5-dimethylhexyl radical have too low a metabolic degradability, sufficiently high degradability can be achieved and ensured in that a quasi "metabolic predetermined breaking point" is introduced into the molecule. In this variant, a so-called intramembrane spacer is introduced between the two mentioned ω-position C-atoms, said spacer comprising one or more C—, O— or N-atoms (FIG. 2*a*).

In the simplest case, this spacer can comprise at least one heteroatom, such as e.g. oxygen or nitrogen, possibly in combination with a few C-atoms. Preferred chain lengths for the intramembrane spacer are 1-4 atoms.

During synthesis of such a "head-to-head" dimer, the operation cannot start from the original cholesterol molecules but from the ω-hydroxy derivative, i.e. 27-hydroxycholesterol (or 26-hydroxycholesterol). The dimerisation via the ω-position carbon atom does not lead here to a pure hydrocarbon chain, as shown in FIG. 2*a*, but to an oxygen bridge with water production which is produced from the two original hydroxyl groups. It comprises one ether-oxygen atom.

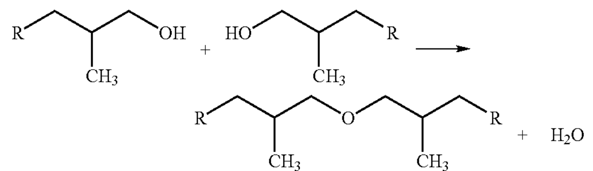

The carbon atoms which are in the direct vicinity of the bridge oxygen atom (the original ω-C-atoms) are now particularly sensitive relative to a hydroxylation, for instance by the cytochrome-$P_{450}$-dependent mixed-functional hydroxylases. A hydroxylation of this type taking place in the direct vicinity of the O-atom leads to the formation of unstable compounds with a semi-acetal structure which degrade into the corresponding reaction products. The reaction product with a ω-position OH group is identical to the starting product 27-hydroxycholesterol.

According to some recent works of medical literature, 27 hydroxycholesterol is suspected of having an atherogenic effect. However an undesired effect of this type is practically of no importance since, as a result of the low metabolic degradation of the cholesterol oligomers, only such a quantity of 27-hydroxycholesterol is released which is negligibly low relative to the quantity present in total in the organism.

The other reaction product is a cholesterol with a ω-position aldehyde function which is further oxidised to form the carboxylic acid group. Hence it becomes obvious that, by means of a (in any case slowly proceeding) biochemical degradation of the described dimeric cholesterol molecules, products are produced which are very similar to the starting compound cholesterol and which, on the basis of the presence of functional groups (on the one hand a —OH group and on the other hand a —COOH group), can be converted very easily into readily water-soluble and easily removeable end products with the help of physiological conjugation reactions.

In the case where the dimerisation of the two cholesterol molecules is intended to lead at the same time to a controllable degree of degradability of the resulting dimeric cholesterol molecule or/and where—for instance for steric reasons—the resulting dimeric cholesterol molecule is intended to have a longer chain than corresponds to the sum of the chain lengths of the monomeric molecules, a longer intramembrane spacer can be incorporated between the two cholesterol molecules. This is achieved for example by the use of glycols, in the simplest case ethylene glycol, for bridging the 27-hydroxycholesterol. In this case, a reaction product is produced which contains two oxygen atoms in the entire chain:

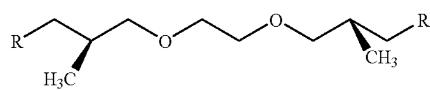

Hence the entire molecule has grown relative to the sum of the two monomeric molecules in practice by the length of the intramembrane spacer —O—$CH_2$—$CH_2$—O—. Because of the two oxygen atoms present in this chain, a readily controllable degradation rate of the entire molecule can be achieved as a result of the ability of the two C-atoms adjacent to the O-atoms to be oxidised.

In this way, due to the choice of a suitable intramembrane spacer, both the entire size of the resulting dimeric cholesterol molecule and the extent of its biochemical degradability can be chosen freely because it is possible to incorporate so-called "metabolic predetermined breaking points" in the intramembrane spacer. However it must be ensured that an intramembrane spacer of more than 1 atom chain length should have no pronounced hydrophilic properties since otherwise the possibility of integration of the dimer into the lipid double membrane could be reduced too greatly.

In an entirely analogous manner as in the case of cholesterol itself, during the dimerisation of the cholesterol sulphate and of the different cholesterol esters respectively, the operation should start with 27 hydroxy compounds which can then be cross-linked respectively by water production to form the corresponding dimers. Again largely analogously to the above-described reactions, this can be effected by formation of a bridge oxygen atom or by insertion of an above-described intradimeric spacer.

An essential aspect of the pathogenesis of the above-mentioned skin changes or skin diseases is the reduced water binding capacity of the skin tissue, in particular in the region of the stratum corneum. Physiologically, the water is not incorporated within but rather between the individual lipid bilayers since a plurality of parallel-disposed lipid layers is present. This is based on the fact that the interior of the lipid bilayer is constructed from strongly hydrophobic molecular components, e.g. comprising fatty acid esters and the predominant component of the cholesterol molecule (or the cholesterol analogues) including the 1,5-dimethylhexyl radical, whilst the medium outwith the lipid bilayer is of a hydrophilic nature. Storage of water in the hydrophobic inner regions of the lipid double membrane is not possible in practice.

The initially mentioned skin changes and diseases are ultimately attributable to the loss of a part of the parallel-disposed lipid bilayers and the hydrophilic intermediate layers disposed between these bilayers which leads in particular to a loss of the water binding capacity. The aim of the therapeutic measures in these diseases is hence not only reconstruction and stabilisation of the lipid bilayers themselves, as is effected with the help of the above-described dimers of cholesterol and its analogues but in addition also the construction and stabilisation of the multilamellar lipid structures with the hydrophilic intermediate layers which are situated therebetween and are ultimately of crucial importance for the water binding capacity of the skin.

This aim is achieved in that at least two of the above-mentioned dimers of cholesterol or its analogues are cross-linked covalently. In contrast to the above-described formation of dimeric cholesterol molecules by producing a covalent bond in the hydrophobic range of the cholesterol, i.e. at the ω-position C-atom of the 1,5-dimethylhexyl radical, the covalent bonding of two dimers of cholesterol or its analogues is effected according to a different principle:

1. The cross-linking of two dimers of cholesterol or its analogues is effected in the hydrophilic region of the relevant molecules. As can be deduced from FIG. 1, a reactive OH group is respectively available in the hydrophilic end of the cholesterol molecule, on which the construction of larger molecules, comprising at least two cholesterol dimers, can be effected.

In the case of cholesterol sulphate, this reactive cross-linking point is provided by the second acid function of the sulphuric acid which is coupled to the cholesterol.

In the case of the cholesterol esters, a reactive bonding point for the linkage of a plurality of dimers is initially not present. It can however be easily produced in that the carboxylic acid present in the cholesterol esters (with any chain length) carries an end-position OH group. Dimeric cholesterol esters can also be constructed in that esterification of two cholesterol molecules is effected with a dicarboxylic acid.
2. Cross-linking of two cholesterol dimers is effected not directly which would be possible with water production by forming an ether grouping. (The existence of a cholesterol ether is described in the literature). Rather it is necessary for physiological reasons to have an intermediate space produced of a defined minimum size between respectively two forming parallel-disposed lipid layers, in which space water and possibly hydrophilic molecules, possibly also the comparatively large molecule collagen, can be incorporated. The construction of an intermediate space is however possible if and only if the two dimers of cholesterol to be cross-linked (and the analogues thereof, cholesterol sulphate and cholesterol esters) are kept at a spacing by an extramembrane spacer (FIG. 3).

For the above-mentioned reasons—the intermediate space produced by the spacer between two parallel-disposed lipid bilayers must be able to absorb and store water and hydrophilic molecules—the extramembrane spacer should always have hydrophilic properties. However it can be provided according to the present above-mentioned skin disease with a greatly different chain length.

In the following, some examples of structures of extramembrane spacers are intended to be given for the cross-linking of cholesterol dimers, in the case of which respectively one hydrophilic molecule structural element with a different structure and chain length is cross-linked with the OH group which is present respectively in the hydrophilic region of the cholesterol molecule (in the following examples, the cholesterol molecule is designated respectively with R'):

With glycerine as spacer-forming molecule, the following structure of the extramembrane spacer is produced with two ether groupings

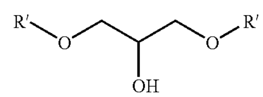

The additional incorporation of two hydroxydicarboxylic acids, such as malic acid or tartaric acid, leads, with formation of two ether bonds and two ester groupings, to an extended strongly hydrophilic extramembrane spacer because of the presence of two free dissociated carboxyl groups:

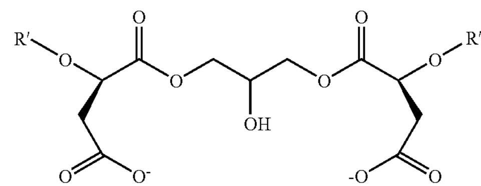

When using two molecules of aspartic acid including the four present carboxyl groups and with formation of four ester groupings, an extended extramembrane spacer is produced which is also strongly hydrophilic because of the presence of two amino groups which can be protonated at physiological pH values:

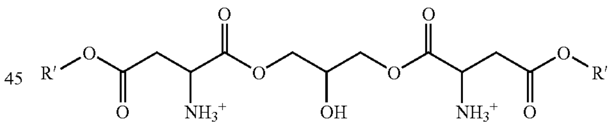

The construction of a urea derivative as structural element of the extramembrane spacer is of particular interest. This is possible by the use of two molecules of an amino dicarboxylic acid, such as e.g. glutamic acid. A relatively long spacer is hereby produced which has a strongly hydrophilic nature, which is provided inter alia by the presence of the two negatively charged carboxyl groups:

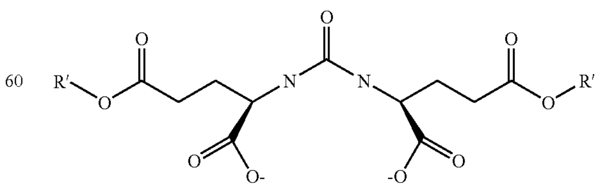

The construction of a urea-analogous structure is therefore of particular interest because urea has a very high water binding capacity which is used today already in the form of urea-containing ointments for the therapy of such skin diseases in which drying of the skin represents an essential feature of the disease (e.g. in the case of dyshidrotic eczema).

There are in practice no limits on the diversity of the spacer structures and the length of the usable extramembrane spacers. The structure just as the chain length can be adapted widely as necessary to the special therapy demands. The incorporation of specific monosaccharides, such as e.g. glucose, is also possible inter alia, which leads in turn to derivatives of physiological substances.

In the case of the cholesterol esters with an "alcoholic" OH group which is in end-position on the carboxylic acid present in the molecule, the linking possibilities, which are the same in principle, of an extramembrane spacer are produced: with an alcoholic OH group of the spacer, cross-linking takes place with formation of an ether grouping, with the COOH group of the spacer cross-linking takes place with formation of an ester function. The structures reproduced above for the incorporation of an extramembrane spacer between two cholesterol dimers applies in the same way also for the incorporation of an extramembrane spacer between two dimers of cholesterol esters. The only difference resides in the fact that now "R" no longer stands for "cholesterol" but for "cholesterol-O—CO-alkyl".

Merely in the case of cholesterol sulphate does a change in this respect occur relative to the two preceding cases, when here the cross-linking of the two dimers is possible exclusively via two OH groups which are present at the end-position on the extramembrane spacer with formation of two sulphuric acid ester groupings. Cross-linking of the sulphuric acid esters with end-position COOH groups of the extramembrane spacer is in practice impossible since the resulting so-called mixed acid anhydrides (comprising sulphuric acid and carboxylic acid) are not sufficiently stable as energy-rich compounds for therapeutic use.

The choice of the mentioned different structures in the extramembrane spacer leads to different biological stabilities and hence to a different degree of the desired degradability of the oligomeric molecules comprising cholesterol and cholesterol analogues, which is intended on the one hand to be below the value for the corresponding monomeric molecules but, on the other hand, is intended not to be entirely missing. Hence a certain controllability of the effective strength and duration of the oligomers comprising cholesterol or cholesterol analogues which are used for the therapy is also provided via this intermolecular spacer structure.

Also in the case of the metabolic degradation of the described oligomeric molecules, in particular the spacers thereof, degradation products are produced which are identical to physiological substances (e.g. amino acids or sugar) or have very great similarity to them so that the probability of undesired side-effects, i.e. toxic effects, is extremely low.

Relative to the dimeric molecules comprising cholesterol or cholesterol analogues, the oligomeric molecules with 4-12 monomers (or 2-6 dimers) in particular tetramers, hexamers or octamers, have a greater capacity to stabilise the structure of the parallel-disposed lipid membrane bilayers. Due to these compounds, the result is the construction of 2 parallel bilayers in the case of tetramers, of 3 parallel bilayers in the case of hexamers, of 4 parallel bilayers in the case of octamers etc., with an increased tendency towards storage of water and hydrophilic molecules of a different size in the spaces between the parallel lipid bilayers.

Oligomeric cholesterol molecules with an uneven number of monomers, in the simplest case i.e. a trimeric molecule comprising cholesterol or cholesterol analogues with an intramembrane and an extramembrane spacer, can certainly be used also for the purposes mentioned here even if they do not have the optimal properties for integration in the present lipid bilayers. In the example of a trimeric molecule, the two molecules connected via an intramembrane spacer would be integrated optimally in a lipid bilayer, whilst the further molecule connected via an extramembrane spacer would merely protrude into the one half of the next lipid bilayer.

A dimeric molecule comprising cholesterol or cholesterol analogues represents a special case, which molecule is connected via an extramembrane spacer (according to the above-indicated variant 2 of the cross-linking during dimerisation). It also applies to this molecule that it can be used perfectly well for the purposes mentioned here even if it has the optimal properties for integration into the present lipid bilayer even less. In this case, both present molecules of cholesterol or cholesterol analogues protrude merely into one half of the respectively adjacent lipid bilayers.

Ultimately, during construction of the dimeric and oligomeric molecules, also so-called hybrid forms are possible. In the simplest case of a dimer, this is for example a molecule which is constructed from a cholesterol monomer and a cholesterol sulphate monomer. Further combination possibilities are: cholesterol monomer+cholesterol ester monomer and cholesterol sulphate monomer+cholesterol ester monomer. The combined use of all three different monomers leads to so-called "hybrid oligomers". As a result of this combination of all three cholesterol components, it is possible to produce preparations for the therapy of skin diseases which have optimal desired proportions or relations of the three components, cholesterol, cholesterol sulphate and cholesterol ester. Such a composition can be orientated for example to the physiological composition of healthy skin in the three mentioned monomers (Hatfield R M and Fung L W (1999): *Biochemistry* 38(2): 784-791).

The invention is explained subsequently in more detail with reference to the Figures. However these are not intended to restrict the present invention to the embodiments shown here.

FIG. 1 shows the arrangement of cholesterol molecules in a typical stable structure of the lipid bilayer of biological membranes. The strongly hydrophobic 1,5-dimethylhexyl radical which is in position 17 of the cholesterol molecule is directed into the interior of the bilayer, whilst the hydrophilic hydroxyl group, in position 3, is directed outwards.

FIG. 2 shows a coupling according to the invention of two cholesterol molecules to form a dimer with formation of a covalent bond (FIG. 2*a*) and by cross-linking with an intramembrane spacer, represented by a rectangle with diagonals (FIG. 2*b*).

FIG. 3 shows, in schematic representation, the structure of a "head-to-head" cholesterol dimer according to the invention by cross-linking with an extramembrane spacer, represented by a long empty rectangle. The dimer is anchored with respectively one monomer in respectively one half of two parallel-disposed lipid bilayers. Only one half of the two adjacent double membranes respectively is represented.

Figure 4:
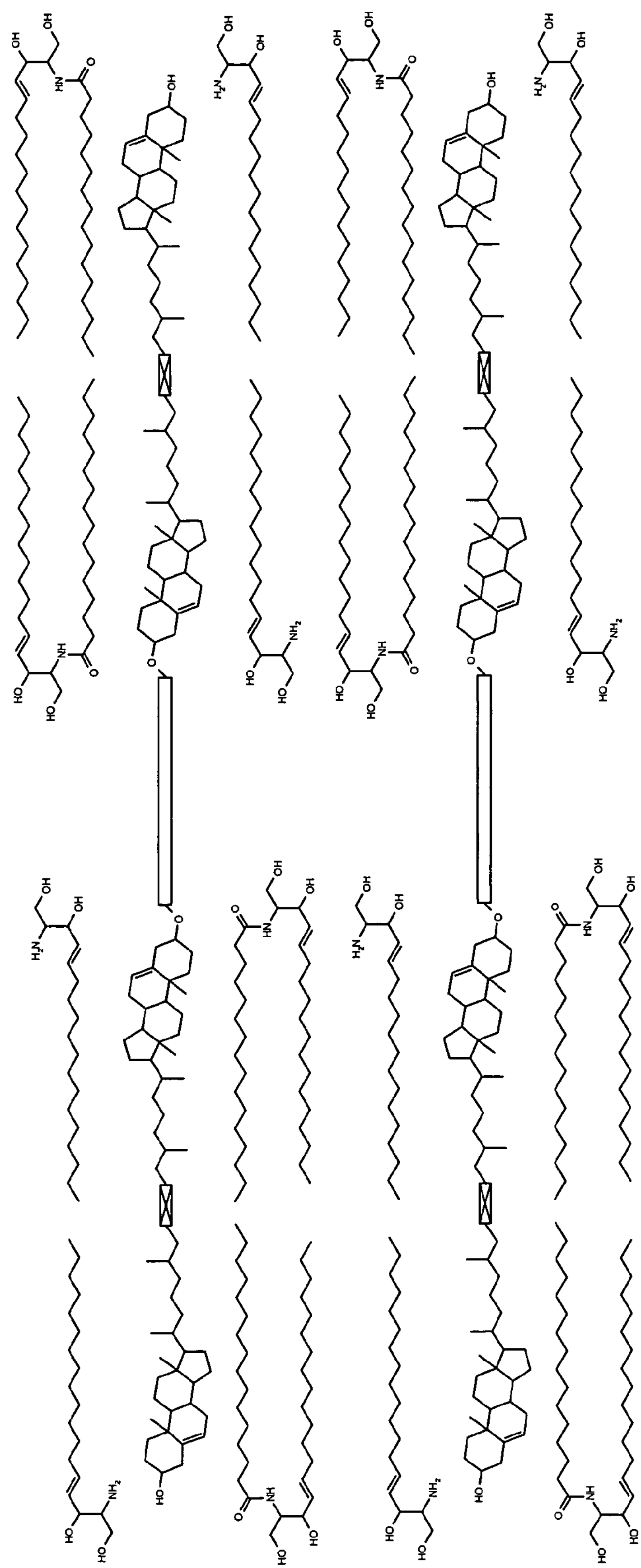

FIG. 4 shows, in schematic representation, the arrangement of tetrameric cholesterol molecules according to the invention, which function as connecting element between two lipid bilayers. Between the two adjacent lipid bilayers there is a hydrophilic intermediate space. The two cholesterol dimers connected in the "tail-to-tail" arrangement, which are in the interior of the membrane, contain an intramembrane spacer (rectangle with diagonals). The two dimers themselves are cross-linked via an extramembrane spacer (empty rectangle) which is located in the hydrophilic intermediate space of the two membranes.

Analogously to the tetrameric compounds shown in FIG. 4, hexamers according to the invention can be incorporated in a similar manner in three parallel-disposed lipid membranes which are separated from each other, octamers in four lipid membranes etc.

Cholesterol oligomers of the described type can be applied in medicine for therapeutic purposes wherever the natural construction of biological membranes is disturbed by pathological processes and, by the use of these oligomeric compounds, stabilisation of the membrane structure and/or a change in the membrane properties is intended to be achieved in the sense of a therapeutic goal (e.g. in order to increase the membrane stability, increase the water binding capacity etc.).

A few examples are mentioned subsequently:

In the case of specific poisonings, which preferentially attack the liver, such as e.g. poisoning with tetrachloromethane (tetrachlorocarbon, "TETRA", $CCl_4$), the lipids of the liver cell membranes are attacked in their structure by radicals. During this process, cholesterol inter alia is also oxidised. The consequence thereof is partial degradation of the lipids and destabilisation of the membrane which leads to partial dissolution of the cell membrane and hence to severe damage to the cell. The supply of the described cholesterol dimers can contribute in such a case of poisoning to significant stabilisation of the membrane of the damaged liver cells.

A change in the lipid composition of nerve cells occurs in the case of a large number of different cases of pathological damage to nerve cells. There are associated herewith inter alia neuronopathy, axonopathy and myelinopathy. As causes for the damage or the degradation of the lipid-rich myelin sheaths, specific exogenous harmful substances are considered, such as e.g. hexachlorophene, isoniazid and organotin compounds.

In the case of myelinopathies, such as for example multiple sclerosis, there are considered for stabilisation of the lipid membranes of the myelin sheaths, because of their specific structure, preferably dimers of cholesterol with relatively short hydrophobic intramembrane spacers between the monomers and also oligomers with relatively short hydrophilic extramembrane spacers.

According to the present state of knowledge, skin diseases are one of the main areas for use of the mentioned oligomers of cholesterol, cholesterol sulphate and cholesterol esters, not least because, in the stratum corneum of human skin, cholesterol and its derivatives play an essential role. These possibilities for use are therefore described in detail in the present patent specification.

The invention claimed is:

1. A dimer of two cholesterol monomers selected from the group consisting of cholesterol, cholesterol sulphate and cholesterol esters, the two monomers respectively being bonded to each other covalently via the ω-position carbon atom of the 1,5-dimethylhexyl radical by a hydrophobic spacer or by a bond.

2. A dimer according to claim 1, wherein the hydrophobic spacer contains a glycol as a structural component.

3. A dimer according claim 1, wherein the hydrophobic spacer comprises one or more carbon-, oxygen- and/or nitrogen atoms.

4. A dimer of two cholesterol monomers selected from the group consisting of cholesterol, cholesterol sulphate and cholesterol esters, the two monomers respectively being bonded to each other covalently via their hydroxyl group at position 3 of the cholesterol backbone of a hydrophilic spacer.

5. A dimer according to claim 4, wherein the hydrophilic spacer contains as a structural component, glycerine, a hydroxylated dicarboxylic acid, an amino acid, and/or a carbohydrate component.

6. A dimer according to claim 4, wherein the hydrophilic spacer contains a monosaccharide, disaccharide, oligosaccharide, mevalonic acid, and/or pyrrolidone carboxylic acid.

7. A pharmaceutical composition suitable as a human or veterinary drug containing a dimer according to claim 1, and a pharmaceutically acceptable carrier.

8. A cosmetic or body care agent containing a dimer according to claim 1, and a cosmetically or body care acceptable carrier.

* * * * *